US008902250B2

(12) United States Patent
Keuenhof (10) Patent No.: US 8,902,250 B2
(45) Date of Patent: Dec. 2, 2014

(54) INPUT DEVICE FOR THE REPRESENTATION OF MEDICAL IMAGES ON A LARGE DISPLAY

(75) Inventor: Bernd Keuenhof, Kleinsendelbach (DE)

(73) Assignee: Siemens Aktiengesellschaft, München (DE)

(*) Notice: Subject to any disclaimer, the term of this patent is extended or adjusted under 35 U.S.C. 154(b) by 645 days.

(21) Appl. No.: 12/272,402

(22) Filed: Nov. 17, 2008

(65) Prior Publication Data
US 2009/0135202 A1 May 28, 2009

(30) Foreign Application Priority Data

Nov. 23, 2007 (DE) .................... 10 2007 056 434

(51) Int. Cl.
G09G 5/00 (2006.01)
G06F 19/00 (2011.01)
G06F 3/14 (2006.01)
G09G 5/14 (2006.01)

(52) U.S. Cl.
CPC .......... G06F 19/321 (2013.01); G09G 2340/14 (2013.01); G09G 2340/12 (2013.01); G09G 2380/08 (2013.01); G09G 5/14 (2013.01); G06F 3/1446 (2013.01); G06F 3/1431 (2013.01)
USPC ............ 345/629; 345/619; 715/788; 715/789

(58) Field of Classification Search
USPC ............ 345/619, 629, 1.1; 715/788, 789, 744
See application file for complete search history.

(56) References Cited

U.S. PATENT DOCUMENTS

| 5,805,118 A | * | 9/1998 | Mishra et al. ................ 715/744 |
| 5,877,819 A | * | 3/1999 | Branson ........................ 348/701 |
| 5,987,345 A | * | 11/1999 | Engelmann et al. .......... 345/636 |
| 6,707,476 B1 | * | 3/2004 | Hochstedler .................. 715/744 |
| 2007/0203748 A1 | | 8/2007 | Rothpearl et al. |
| 2008/0008401 A1 | * | 1/2008 | Zhu et al. ...................... 382/294 |
| 2009/0213034 A1 | * | 8/2009 | Wu et al. ........................ 345/1.1 |

OTHER PUBLICATIONS

German Office Action dated Apr. 14, 2008 for corresponding German Patent Application No. 102007056434.3-53 with English translation.
Chinese Office Action dated Dec. 19, 2011 for corresponding Chinese Patent Application No. 200810181837.5 with English translation.
Eichelberg et al., "User Manual, DICOMscope 3.5.1.." Jul. 23, 2001, OTech Inc. (USA) Institute for Microtherapy (Germany) Kuratorium OFFIS e.V. (Germany), pp. 1-79 eHB; United States.
Bonfiglio et al., "10.4: New Display Solutions for the Image-Centric Era of Healthcare," SID Symposium Digest of Technical Papers, vol. 38, Issue 1, pp. 123-126 (2007).
Handbook, "A Practical Guide to DICOM," Toshiba America Medical Systems, 16 pages, 2001 (http://www.medical.toshiba.com).

* cited by examiner

Primary Examiner — Chante Harrison
(74) Attorney, Agent, or Firm — Lempia Summerfield Katz LLC (57) ABSTRACT

An input device for the selection of medical images for representation on a large display is provided. An image configuration can be selected for display on the large display from a plurality of image configurations by the input device. Selecting the image configuration enables a plurality of images for display on the large display and their arrangement on the display to be determined. The image configuration is created according to requirements of a medical workflow associated with the image configuration. A representation suitable for a medical workflow may be displayed on the large display.

20 Claims, 6 Drawing Sheets

FIG 1

| Live Sub A | Live Nat Ref A | Ref 2 A |
|---|---|---|
| Live SUB B | Live Nat Ref B | Ref 2 B |
| ECG data | | System control |

Biplane Configuration 1
Neuro: with Live Sub, Live Nat/Ref, Ref 2

FIG 2

| Live Sub A | Ref 2 A | Syngo Workplace |
|---|---|---|
| Live SUB B | Ref 2 B | ECG |
| System control | | Taskbar |

Biplane Configuration 2
Neuro: with Live Sub, Ref 2, Syngo Workplace, ECG

INPUT DEVICE FOR THE REPRESENTATION OF MEDICAL IMAGES ON A LARGE DISPLAY

This patent document claims the benefit of German Patent Application No. DE 10 2007 056 434.3 filed on Nov. 23, 2007, which is hereby incorporated by reference.

BACKGROUND

The present embodiments relate to the selection of medical images for representation on a large display.

During medical examinations in hospitals, a plurality of representations and/or images may be used to capture (illustrate) the part of the body under examination. Several different perspectives can be represented, for example, by a medical imaging procedure. Different imaging techniques or procedures (e.g. X-ray, computed tomography, ultrasound, magnetic resonance tomography, video, scattering of laser beams, etc.) are combined, in order to obtain as much information as possible about the patient's health problems. Several images may be used when recorded images are superimposed under various conditions (e.g. before and after absorption of contrast medium) in order to obtain the most high-contrast representation (e.g., using a difference method).

Different medical images are represented on individual, dedicated image reproduction devices. Accordingly, a separate image reproduction device is required for each video (e.g., graphics card) output of a medical imaging system. An X-ray system examination unit may have eight or even more image reproduction devices in an examination room, including color displays for echocardiogram (ECG) and ultrasound.

A solution with many displays is confusing, inflexible and not easy to scale up. The publication "New Display Solutions for the Image-Centric Era of Healthcare" by S. Bonfiglio and L. Albani in SID Symposium Digest of Technical Papers—May 2007—Volume 38, Issue 1, pp. 123-126 discloses the representation of a plurality of medical images on a large display. The display is used to manage the examination with one display per examination unit. The publication discloses an input device by which images to be displayed on a large display can be selected from a plurality of possible medical images. The input device (tablet PC) has a display, which includes a first region with images that can be selected and a second region in which the images represented on the large display are shown. By moving an image from the first region to the second region, the image is selected and it is then represented on the large display.

With a plurality of images or image streams it is not always easy to arrange these optimally on a large display. The arrangement would generally have to be carried out by the physician because this must also be carried out according to medical criteria.

SUMMARY AND DESCRIPTION

The present embodiments may obviate one or more of the problems or drawbacks inherent in the related art. For example, in one embodiment, the representation of medical image combinations on a large display is simplified.

In one embodiment, an input device selects medical images for representation on a large display. As used herein, images may include image streams, for example, image streams that are continuously recorded by a medical procedure and represented on the large display. An image configuration may be selected from a plurality of image configurations by the input device for display on the large display (e.g. by representation of image configurations that can be selected on a display of the input device and selected by clicking or moving). By selecting the image configurations, a plurality of images or image streams for display on the large display and their arrangement on the display are determined. An image configuration may include a combination of static images and image streams. The elements or components of the image configuration (e.g. static images, image streams, representation of patient data, status messages or workflow information) are combined and arranged according to the requirements of the medical examination or treatment associated with the image configuration according to the requirements of a medical workflow. The image configurations may be redesigned, adapted, or tailored individually to the medical workflows and the provision of technical equipment for the respective installation location or hospital.

The selection and configuration for representation on the large display may be simplified. The large display or large screen may be an image reproduction device, a display, a monitor, a screen, or a display or screen that allows the simultaneous display of at least two images or image streams of sufficient size and quality in terms of their technical features (e.g., resolution, light and dimensions) for diagnostic or therapeutic applications in hospitals. A monitor having a resolution of 4 megapixels to over 8 megapixels and a screen size from 30" to 64" may be used as a large display in a hospital.

In one embodiment, physician time is saved and selection and arrangement of the representation on the large display is improved by allowing configurations already predetermined and optimized for medical purposes to be selected. The physician can choose the configuration which is most suited to the medical procedure. The physician is not required to give any thought to the appropriate representation on the large display. The physician merely needs to select the image configuration corresponding to the medical examination or treatment in order to obtain a suitable representation.

In one embodiment, the selected configuration may be adapted or processed by display on the input device, for example, by moving images or image streams, separating and removing portions of images and image streams, or combining them in a different way (e.g. by conventional input devices such as PC mouse or touch-sensitive input pen). The physician may change the representation on the large display according to his own preferences. Rules may be predetermined as to which changes are permissible. For example, software may be used to check whether the change is compatible with the formats used. Essential elements, for example, can be defined by image configurations which cannot be removed manually, (e.g. to prevent the hiding of ECG data essential for a treatment). If the changes are not permissible, an error message may be generated.

In order to increase the number of selectable image configurations, the image configurations may be reproduced on an input device display for a display of subsets of the possible image configurations. A subset of image configurations may be selected for display on the input device based on the input device (e.g. scrolling or via a topic menu). The image configuration to be used may be selected from the subset.

In one embodiment, a medical display system includes an input device, a control device for adapting images and image streams according to a selected image configuration for display on a large display, and a large display.

DETAILED DESCRIPTION

Figure 1:
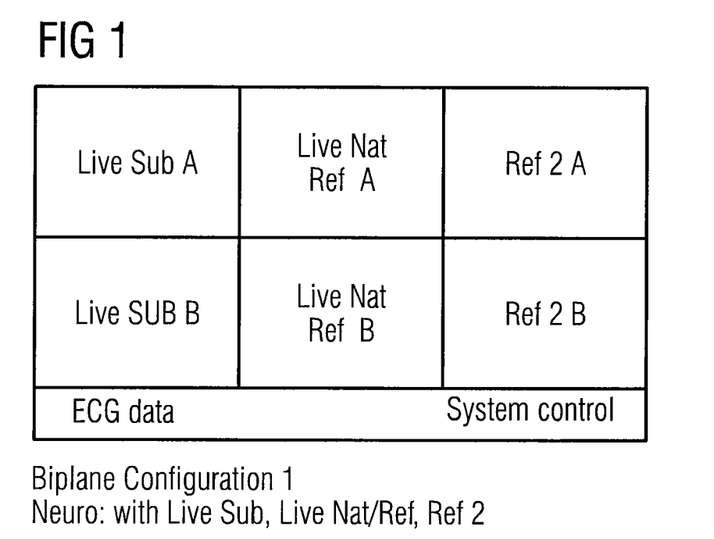
FIG. 1 shows a first image configuration.

FIG. 1 illustrates an image configuration (compilation) having six images represented on a large display. The six images are labeled Live Sub A, Live Sub B, Live Nat Ref A, Live Nat Ref B, Ref 2 A, and Ref 2 B. Live Sub A and Live Sub B are subtraction images. Live Nat Ref A and Live Nat Ref B are unprocessed recordings. Ref 2 A and Ref 2 B are reference images.

One such image compilation is used, for example, in an angiography examination. In angiography, vessels are examined using X-ray recordings. For this purpose a radioactive contrast medium is fed into the vessels and an X-ray is performed. A contrast is achieved by removing the background of the X-ray recording prior to use of the contrast medium, so that only the vessels can still be seen (e.g., in a difference image). A recording is obtained prior to the administering of the contrast medium (e.g., Ref 2 A und Ref 2 B), which is superimposed by the recording after administering of the contrast medium (e.g., Live Nat Ref A und Live Nat Ref B) for removal of the background, in order to generate a difference recording (e.g., Live Sub A und Live Sub B), in which essentially only the vessels are still represented.

Figure 2:
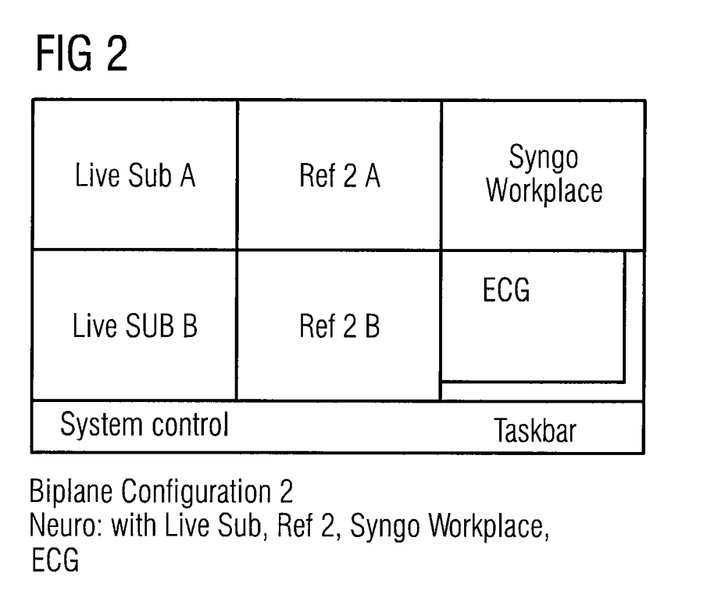
FIG. 2 shows a second image configuration.

In the image configuration, a strip (bar) is provided at the bottom edge of the large display. ECG data and information on system control may be shown in the strip (bar). The image configuration shown in FIG. 2 is distinguished in that the two images on the right-hand side of FIG. 1 are moved into the middle. System-related information (Syngo Workplace) and ECG data are shown and displayed in the two images on the right-hand side of FIG. 1.

Figure 3:
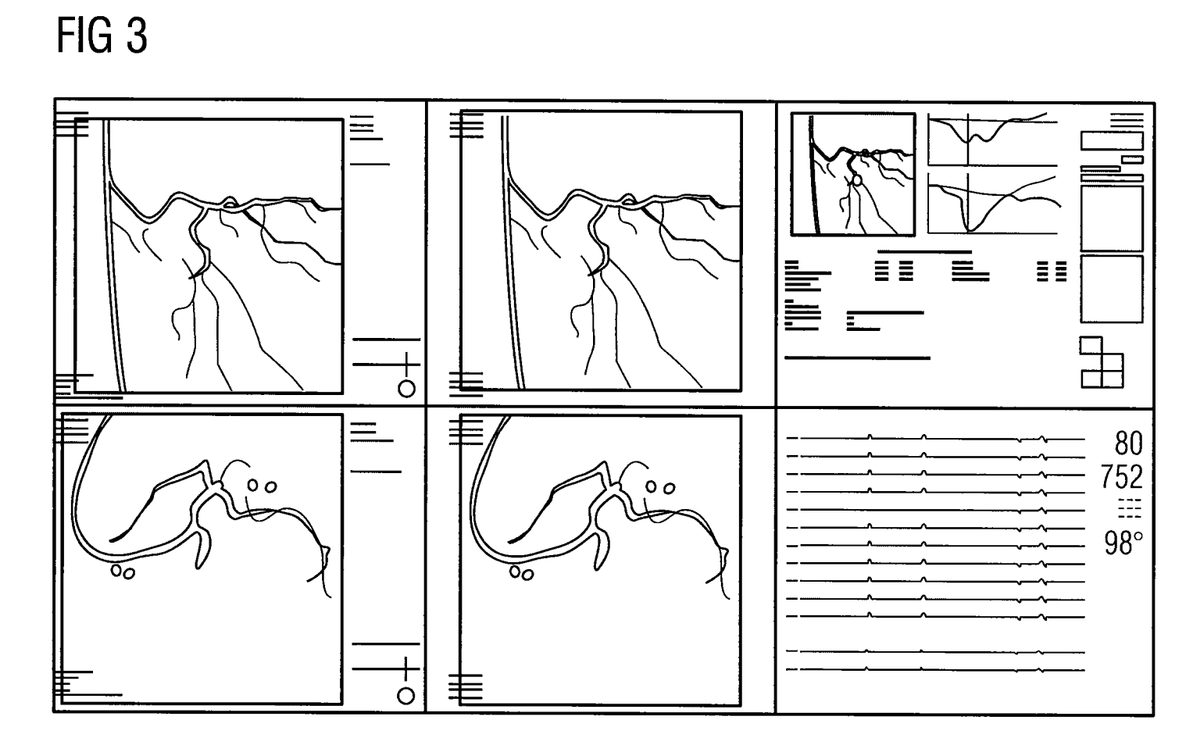
FIG. 3 shows a representation on a large display.

FIG. 3 shows the representation of an image configuration on a large display. On the left-hand side are four images, which show angiographically recorded vessels. On the right, additional relevant information for the workflow is displayed, such as ECG curves.

Figure 4:
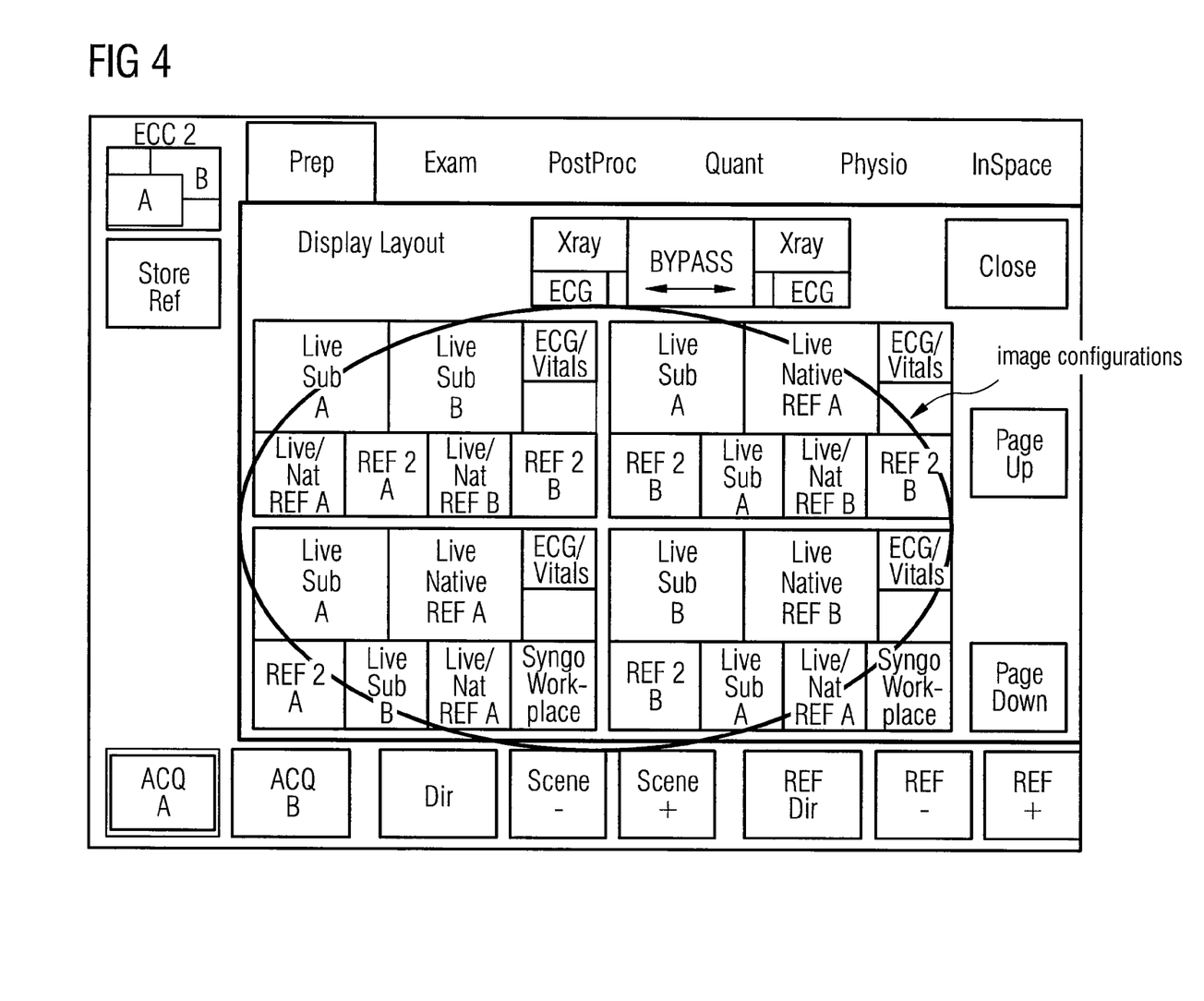
FIG. 4 shows an input device display.

FIG. 4 shows selection of an image configuration by making a selection at an operator console or an input device. FIG. 4 shows four image configurations, whereby the selected image configurations are highlighted. The physician undertaking the treatment can easily select one of the image configurations, for example, by clicking on it or touching it and the configuration chosen is then optically accentuated.

Figure 5:
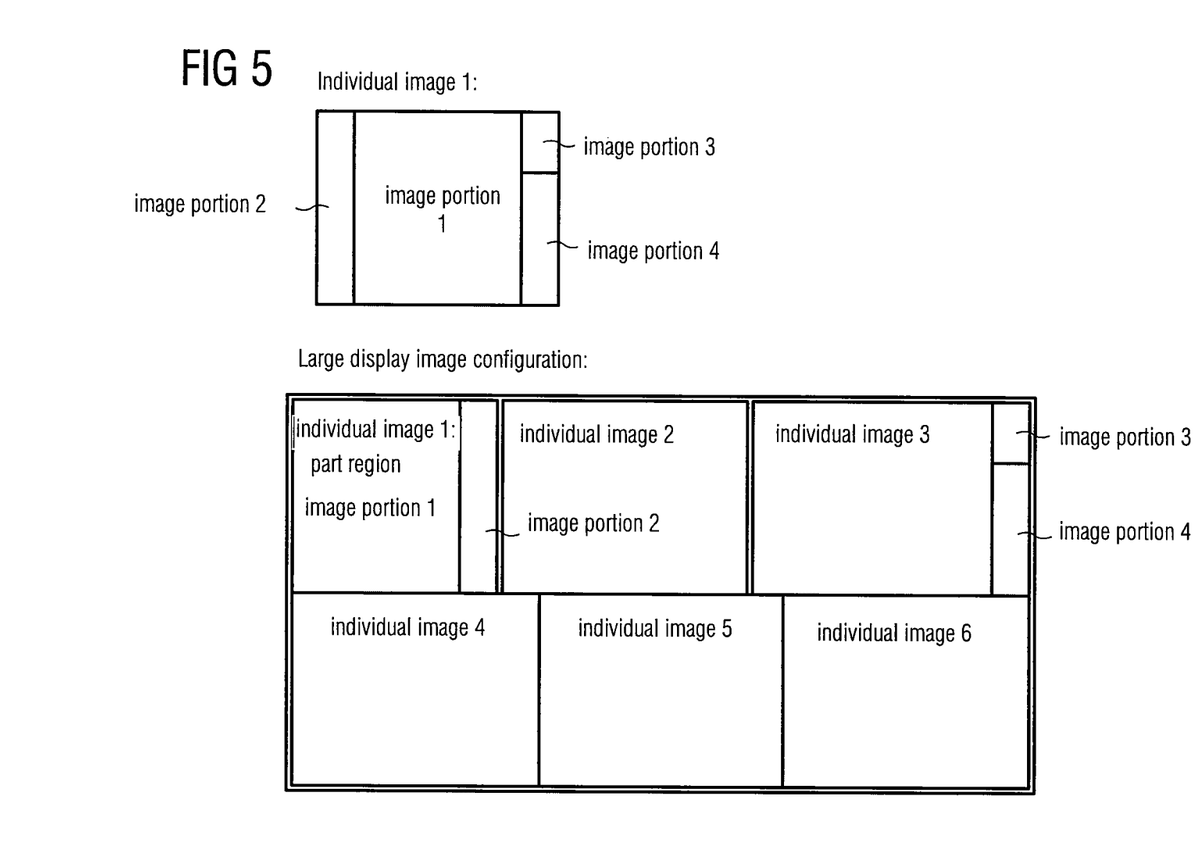
FIG. 5 shows the processing of an individual image for adaptation of an image configuration.
Figure 6:
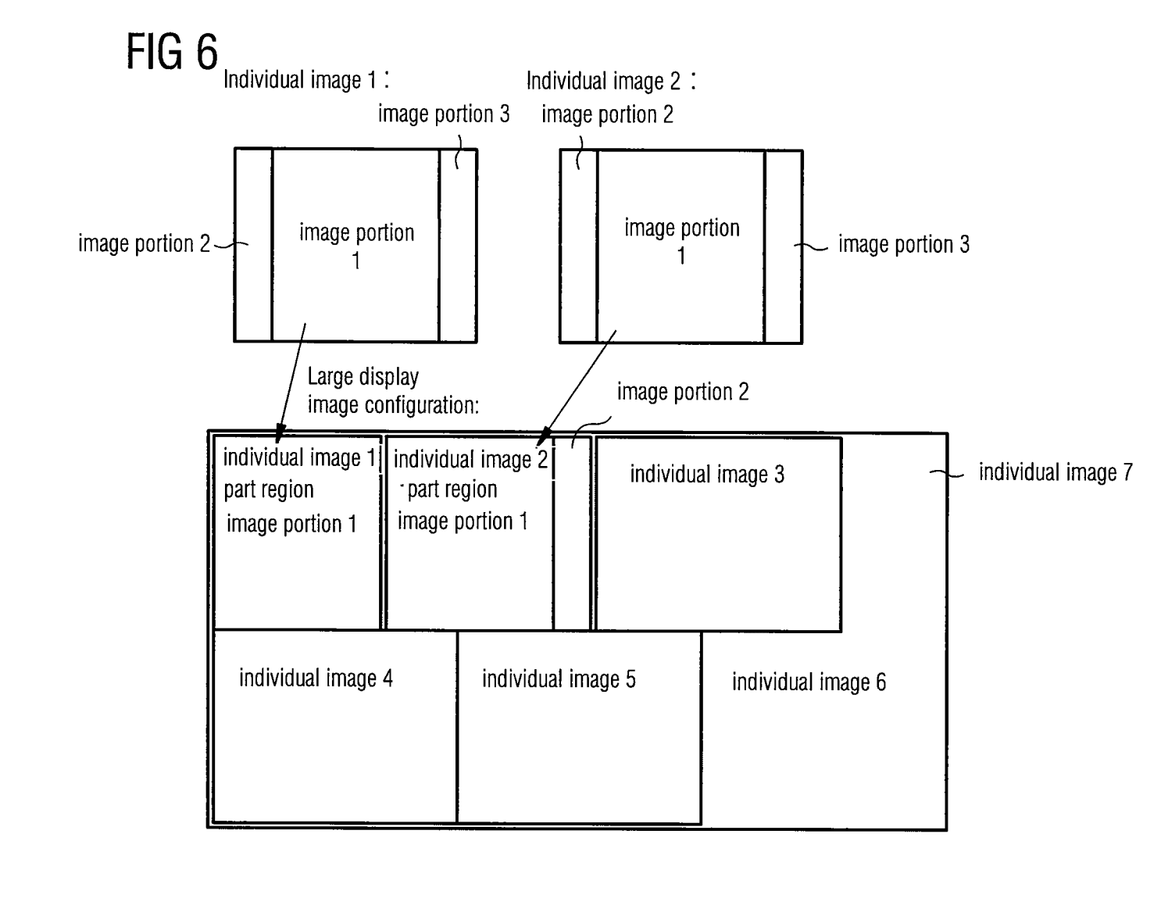
FIG. 6 shows the processing of two individual images of an image configuration.

FIG. 5 shows an individual image at the top. The individual image is divided into four part regions. The division is, for example, performed by the physician by an input device, such as a mouse or optical pen with which a separating line is drawn. On the large display image configuration (below) the part regions or image portions 3 and 4 are separated from the other image portions located on the right on the outside edge. The image illustrates subdividing individual images into part regions and enabling the part regions to be moved. As shown in FIG. 6, the part regions can also be removed from the image displayed on the large display. In the figure, the image portions 2 and 3 of the first individual image and the image portion 3 of the second individual image are removed, in order to create space for the representation of the individual image 7.

Figure 7:
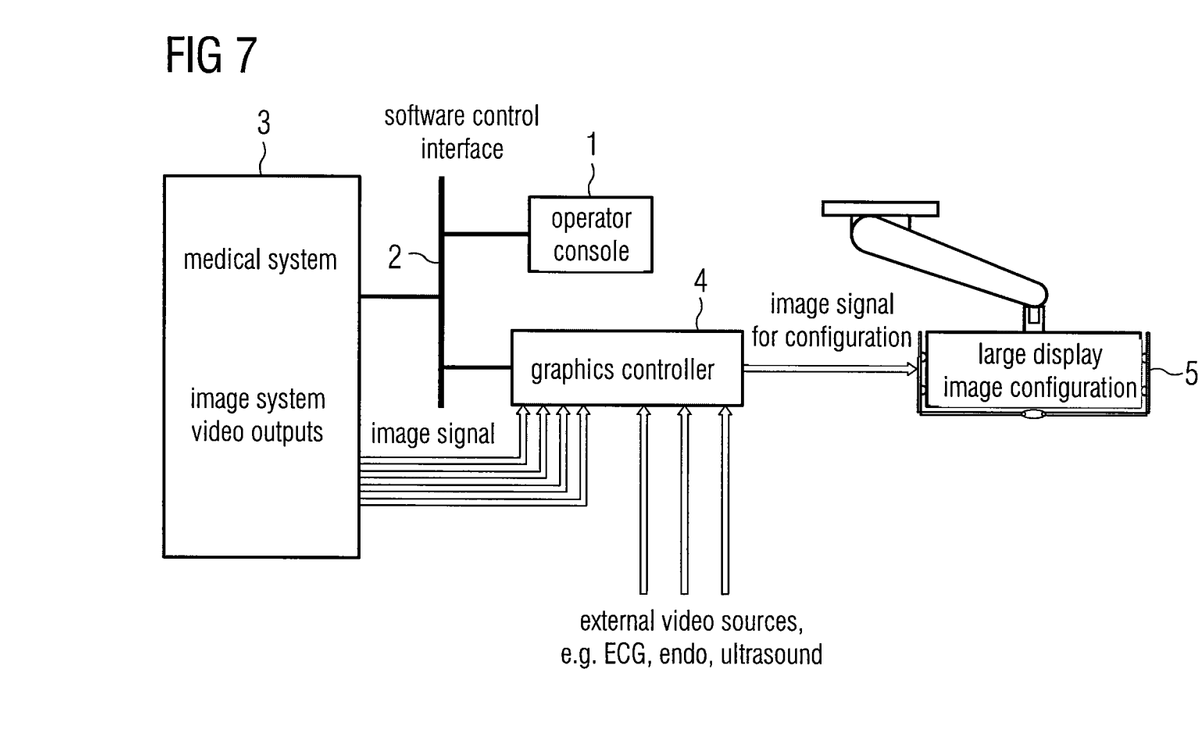
FIG. 7 shows one embodiment of a medical display system

FIG. 7 shows a system for representation of image configurations on a large display. Image configurations may be selected by an operator console 1, which is connected via a software control interface 2 to a medical system 3 and to a graphics controller 4 for display on a large display 5. The operator console 1 is used for the operation and/or control of the medical system 3. The medical system 3 may be, for example, an angiography system by which angiographic images are generated. The images are transmitted to the graphics controller 4. Several inputs are provided in order to be able to transmit a plurality of images to be displayed from the angiography system (e.g. reference images and difference images) to the graphics controller 4 separately.

An image configuration is selected by the input device, for example, the operator console 1. The image configuration is transmitted to the graphics controller 4. The graphics controller 4 includes inputs to external video sources, for example, ECG, endoscopy, and ultrasound. The external video sources may be referenced through image configurations, for example, for representation on the large display 5. The graphics controller 4 has an adaptation device that compiles (generates) an image according to the selected image configuration and possibly other control information and transmits a corresponding image signal to the large display 5.

Additional control information may be specified by user input at the operator console 1. Another possibility is the automatic generation of control information for compilation of the image by the graphics controller 4 by programs that are responsible for adaptation of image configuration displayed on the large display according to the treatment or examination workflow or process.

While the invention has been described above by reference to various embodiments, it should be understood that many changes and modifications can be made without departing from the scope of the invention. For example, although the embodiments were discussed in conjunction with a particle therapy system, the same problems and solutions arise in photon therapy as well. It is therefore intended that the foregoing detailed description be regarded as illustrative rather than limiting, and that it be understood that it is the following claims, including all equivalents, that are intended to define the spirit and scope of this invention.

The invention claimed is:

1. An apparatus comprising:
   an input device for selection of medical images for representation on a large display, the input device being operable to:
      select an image configuration from a plurality of image configurations for display on the large display, the selected image configuration including a plurality of images combined and arranged according to requirements of a medical examination or a treatment associated with the selected image configuration, and for display on the large display, and
   a graphics controller comprising:
      a plurality of inputs each connected to a respective one of a plurality of external video sources, and
      an adaptation device that compiles an image from the plurality of inputs according to the selected image configuration and transmits a corresponding image signal to the large display,
   wherein the input device is further operable to transmit the selected image configuration to the graphics controller upon selection at the input device,
   wherein the input device is operable to adapt the selected image configuration based on user input, wherein the input device includes criteria that must be satisfied to permit the adaptation of the image configuration by the user, the adaptation of the image configuration comprising moving one or more images of the plurality of images within the selected image configuration, separating a portion of an image of the plurality of images and moving the portion of the image, separating and removing the portion of the image, or combining images of the plurality of images, the criteria being one or more pre-determined rules that define permissible adaptations, wherein the input device is configured to determine whether the adaptation is permitted under the one or more pre-determined rules of the criteria, and prevent the adaptation when the adaptation is not permitted under the one or more pre-determined rules of the criteria, wherein the selected image configuration comprises one or more elements defined as essential, wherein the input device is configured to prevent removal of the one or more elements defined as essential within the selected image configuration, and wherein the one or more elements defined as essential comprise ECG data.

2. The apparatus as claimed in claim 1, wherein the selected image configuration is displayed on a display of the input device and is adapted by the input device by changing the image configuration displayed on the display.

3. The apparatus as claimed in claim 2, wherein the image configuration is adapted by cutting out a part region of an image and moving or removing the part region.

4. The apparatus as claimed in claim 2, wherein the image configuration is adapted by cutting out a part region of an image of the plurality of images and moving or removing that region, the part region selected by a physician.

5. The apparatus as claimed in claim 1, further comprising an internal or external memory that is operable to store a plurality of image configurations that are selected by the input device, and the plurality of image configurations from which the image configuration is to be selected are represented on a display of the input device, wherein by a function of the input device, a subset of image configurations is selected for the representation.

6. The apparatus as claimed in claim 1, wherein the input device is operable to check that the adaptation of the image configuration has neither been performed nor output when the criteria has not been satisfied and the adaptation is not permitted.

7. The apparatus as claimed in claim 6, wherein the input device is configured to generate an error message when the adaptation is not permitted.

8. The apparatus as claimed in claim 1, wherein the compiled image includes at least one live image stream and at least one static image.

9. The apparatus as claimed in claim 1, wherein the one or more pre-determined rules define one or more images of the plurality of images that are necessary for the medical examination or treatment and cannot be removed.

10. The apparatus as claimed in claim 1, wherein the selected image configuration includes one or more portions of one or more images of the plurality of images, the one or more portions selected by a physician.

11. The apparatus as claimed in claim 1, wherein the one or more pre-determined rules define a format of each of the plurality of images that the adaptation is to be compatible with and one or more images of the plurality of images that are necessary for the medical examination or treatment and cannot be removed.

12. The apparatus as claimed in claim 11, wherein the input device is operable to check that the adaptation of the image configuration has neither been performed nor output when the criteria has not been satisfied and the adaptation is not permitted.

13. The apparatus as claimed in claim 1, wherein the input device is operable to check that the user adaptation of the image configuration has been performed by the adaptation device and has been output to the large display when the criteria has been satisfied and the adaptation is permitted.

14. A medical display system having:
an input device operable to receive a selected image configuration of a plurality of image configurations, the selected image configuration including a plurality of images,
a display,
a plurality of inputs each connected to a respective one of a plurality of external video sources, and
an adaptation device that compiles an image from the plurality of inputs according to the selected image configuration and transmits a corresponding image signal to the display,
wherein the input device is operable to adapt the selected image configuration based on user input,
wherein the input device includes criteria that must be satisfied to permit the adaptation of the image configuration by the user, the adaptation of the image configuration comprising moving one or more images of the plurality of images within the selected image configuration, separating a portion of an image of the plurality of images and moving the portion of the image, separating and removing the portion of the image, or combining images of the plurality of images, the criteria being one or more pre-determined rules that define permissible adaptations,
wherein the input device is configured to determine whether the adaptation is permitted under the one or more pre-determined rules of the criteria, and prevent the adaptation when the adaptation is not permitted under the one or more pre-determined rules of the criteria,
wherein the selected image configuration comprises one or more elements defined as essential,
wherein the input device is configured to prevent removal of the one or more elements defined as essential within the selected image configuration, and
wherein the one or more elements defined as essential comprise ECG data.

15. The medical display system as claimed in claim 14, wherein the plurality of images in the selected image configuration are combined and arranged according to requirements of a medical examination or a treatment associated with the selected image configuration.

16. The medical display system as claimed in claim 14, wherein the selected image configuration is displayed on a display of the input device and is adapted by the input device by changing the image configuration displayed on the display of the input device.

17. The medical display system as claimed in claim 16, wherein the image configuration is adapted by cutting out a part region of an image and moving or removing the part region.

18. The medical display system as claimed in claim 14, further comprising an internal or external memory that is operable to store a plurality of image configurations that are selected by the input device, and the plurality of image configurations from which the image configuration is to be selected are represented on a display of the input device, wherein by a function of the input device, a subset of image configurations is selected for the representation.

19. The medical display system of claim 14, wherein the input device is operable to check that the user adaptation of the image configuration has been performed and has been output to the display when the criteria has been satisfied and the adaptation is permitted.

20. An apparatus comprising:

an input device for selection of medical images for representation on a large display, the input device being operable to:

select an image configuration from a plurality of image configurations for display on the large display, the selected image configuration including a plurality of images combined and arranged according to requirements of a medical examination or a treatment associated with the selected image configuration, and for display on the large display, and a graphics controller comprising:

a plurality of inputs each connected to a respective one of a plurality of external video sources, and an adaptation device that compiles an image from the plurality of inputs according to the selected image configuration and transmits a corresponding image signal to the large display, wherein the input device is further operable to transmit the selected image configuration to the graphics controller upon selection at the input device, wherein the input device is operable to adapt the selected image configuration based on user input, wherein the selected image configuration is displayed on a display of the input device and is adapted by the input device by changing the image configuration displayed on the display, wherein the input device includes criteria that must be satisfied to permit the adaptation of the image configuration by the user, the criteria being one or more pre-determined rules that define permissible adaptations, the one or more pre-determined rules defining one or more elements of the plurality of images that are necessary for the medical examination or the treatment and cannot be removed, wherein, when the criteria is satisfied and the user adaptation is permitted, the selected image configuration is adapted by moving one or more images of the plurality of images within the selected image configuration, separating a portion of an image of the plurality of images and moving the portion of the image, separating and removing the portion of the image, or combining images of the plurality of images, wherein the selected image configuration comprises one or more elements defined as essential, wherein the input device is configured to prevent removal of the one or more elements defined as essential within the selected image configuration, and wherein the one or more elements defined as essential comprise ECG data.

* * * * *